US008106110B2

(12) United States Patent
Suh et al.

(10) Patent No.: US 8,106,110 B2
(45) Date of Patent: Jan. 31, 2012

(54) DUAL APPLICATION MODE SELF-ETCH DENTAL ADHESIVES COMPATIBLE WITH SELF-CURED AND DUAL-CURED COMPOSITES

(75) Inventors: Byoung Suh, Oak Brook, IL (US); Rui Yin, Buffalo Grove, IL (US); Michelle Schiltz-Taing, Carpentersville, IL (US)

(73) Assignee: Bisco, Inc., Schaumburg, IL (US)

( * ) Notice: Subject to any disclaimer, the term of this patent is extended or adjusted under 35 U.S.C. 154(b) by 781 days.

(21) Appl. No.: 12/021,788

(22) Filed: Jan. 29, 2008

(65) Prior Publication Data

US 2008/0182922 A1 Jul. 31, 2008

Related U.S. Application Data

(60) Provisional application No. 60/898,013, filed on Jan. 29, 2007.

(51) Int. Cl.
*A61K 6/083* (2006.01)

(52) U.S. Cl. .................................. 523/118; 433/228.1
(58) Field of Classification Search .............. 523/118; 433/228.1

See application file for complete search history.

(56) References Cited

U.S. PATENT DOCUMENTS

| 5,749,733 | A  | * | 5/1998  | Qian et al. ............... 433/228.1 |
| 6,288,138 | B1 | * | 9/2001  | Yamamoto et al. ........... 523/118 |
| 7,090,722 | B2 | * | 8/2006  | Budd et al. ................... 106/35 |
| 7,250,452 | B2 | * | 7/2007  | Falsafi et al. ................ 523/115 |
| 7,452,924 | B2 | * | 11/2008 | Aasen et al. ................ 523/116 |
| 7,699,605 | B2 | * | 4/2010  | Aasen et al. ..................... 433/9 |
| 2004/0229973 | A1 | * | 11/2004 | Sang et al. .................... 523/118 |

* cited by examiner

*Primary Examiner* — Tae H Yoon
(74) *Attorney, Agent, or Firm* — Ice Miller LLP

(57) ABSTRACT

The present application relates to a dental primer adhesive system that is capable of being used as either a one-step or two-step self-etch dental primer and is compatible with self-cure composites and dual-cure composites with reduced permeability.

12 Claims, No Drawings

DUAL APPLICATION MODE SELF-ETCH DENTAL ADHESIVES COMPATIBLE WITH SELF-CURED AND DUAL-CURED COMPOSITES

PRIORITY

The present application claims priority to U.S. Provisional Patent Application No. 60/898,013 field Jan. 29, 2007, the contents of which are incorporated by reference herein.

BACKGROUND

Advances in dental restorative techniques include the use of various materials such as composite resins to effect tooth filling or other restorative processes. Other advances include the use of dental components such as thin wire braces and other types of dental components made of metal, ceramics, resins or other bio-compatible substances. Depending on the clinical application, such restoratives and components may be applied directly to the tooth dentin and/or enamel, or may be applied to other bio-compatible substrates such as metals, ceramics, resins, amalgams, or other restorative materials which may already exist in the patient and/or are to be added as part of the clinical treatment.

Common to the foregoing materials and techniques is the need for bonding systems to enhance the bonding of the restorative or other dental component to the chosen dental substrate. Ideally, such enhancement would provide bond strengths which approach the strength of the underlying substrates. In addition, ideal bonding systems would also be simple for the dental professional to use in a manner which requires a minimum of time for the patient in the chair.

Several bonding systems and techniques have been reported in the literature which have achieved some, but not all of the above-stated goals. Such bonding systems can be divided into three general categories, multiple-component primer systems, two component primer systems, and single-component primer systems.

A. Multiple Component Bonding Systems

A general discussion of multiple-component bonding systems and their predecessors is set out in Suh, "All-Bond—Fourth Generation Dentin Bonding System," J. Esthetic Dentistry, Vol. 3, No. 4, pp. 139-147 (July-August, 1991) and in Bowen U.S. Pat. No. 5,270,351 at Col. 1, lines 29-Col. 2, line 36 and Col. 2, lines 54-64, the disclosures of which are hereby incorporated by reference. Briefly summarized, the early generation bonding systems generally disclosed at Col. 1 and 2 of the '351 patent began with simple pretreatment of the dental substrate with mordents and/or acidic solutions before application of the dental restorative or component. Such systems, while simple to use, did not provide high bond strengths on substrates such as tooth dentin.

Those low bond strengths led to the development of the multiple-component bonding systems discussed at Col. 2 of the '351 patent and discussed in detail in the J. Esthetic Dentistry article at pp. 139-147. Such systems generally employed the older generation system's first step of pretreatment of tooth dentin or enamel with acidic solutions to decalcify and remove dentin smear layer and to etch tooth enamel (a technique often referred to as "total etch" process, as both dentin and enamel may be etched using a low pH solution). The multi-component systems then employed two or more separate "primer" or "adhesive enhancing" compounds to further enhance bonding between the substrate and the dental restorative. However, the primers in such systems must either (1) be applied separately and sequentially to the dental substrate, or (2) must be mixed together by the dental professional in the office immediately before use on the patient to prevent premature polymerization of the components.

The first type of such multiple-component primer systems is exemplified in Bowen U.S. Pat. Nos. 4,514,527, 4,551,550, 4,558,756 and 4,659,751, and U.S. Pat. No. 4,964,911 Ivson et al., (and related Ibsen et al. U.S. Pat. re 34937) discussed at Col. 2 of the '351 patent. Those earlier patents disclose, inter alia, two or three component primer systems employing the separate steps of treating the dental substrate with (1) an acidic acid solution of inorganic acids, polycarboxylic acids and metal salts of such acids capable of changing valence states, (2) applying a first primer compound comprising N-amylglycine and derivatives such as NTG-GMA (the adduct of N(p-tolyl)glycine and glycidyl methacrylate), NPG (N-phenylglycine), and other amino acids and metal salts thereof to the substrate, followed by (3) applying a second polymerizable adhesive bonding monomer to the substrate comprising PMDM, BDTA-HEMA, 4-META, or other polymerizable acidic monomers disclosed therein and having groups or moieties that do not interfere with polymerization. Although some of those systems report achieving moderate bond strengths for bonding to substrates such as tooth dentin, from about 1600 to about 2500 p.s.i (11-17 Mega Pascals (1 MPa=145 p.s.i.)), such multi-component/multi-step methods are necessarily complicated for the dental professional and time-consuming for the patient.

B. Two-Component Primer Systems

As an alternative to multiple-component primer systems, Bowen and others, including applicant's assignee, Bisco, Inc., have reported development of two-component primer systems. See e.g., Bowen U.S. Pat. Nos. 5,320,886 and 5,270,351, Suh et al. article cited above and U.S. Pat. No. 5,348,988 and Bunker U.S. Pat. No. 4,544,467. Such systems involve steps whereby the dental professional admixes the two primer components immediately prior to application of the mixture to the dental substrate. Immediate application is required in such systems because the primer composition begins to polymerize upon mixing due to the chemical nature of the primer molecules, at least one of which contains ethylenically unsaturated (vinyl) groups whose polymerization is initiated by the tertiary amine group present on the other primer component of the system. The two-component primer bonding systems typically require an acid-etch step to provide a secure bond between the dentin and/or enamel and the primer, resulting in the so-called "hybrid layer" wherein the dentin/enamel and primer interface with one another.

A different type of a two-component primer bonding system is disclosed in Waknine U.S. Pat. No. 5,276,068. That two-component system comprises a polymerization initiator and a polymerizable compound which are packaged separately. The first step in that system requires application of polymerization initiator alone to the dental substrate. In a second step, the polymerizable compound is applied to the substrate. Polymerization begins when the polymerizable compound comes into contact with the initiator on the substrate surface.

Some of the aforesaid multiple-component primer systems were reported as providing only moderate dentin adhesive bonding strengths. For example, the data included in the Bowen '351 and '886 patents show dentin adhesive bond strengths of from about 10 to about 15 MPa. Moreover, the higher bond strengths reported in the '351 patent were achieved only after an additional step and component, comprising applying an unfilled adhesive resin monomer to the primed substrate before application of the dental restorative composite material, was added to the restorative process. (See '351 patent, Example 1). The Waknine '068 patent also reports relatively low bond strengths in the 10 MPa range and also used an additional step of application of a commercial bonding resin (see Examples 22-23). Bunker et al. reported slightly lower dentin shear bond strengths of between about 5 MPa and 8 MPa (49.3 to 86.5 kg/cm$^2$).

Surprisingly, Suh et al.'s two-component primer system utilizing polymerizable acidic monomer biphenyl dimethacrylate (BPDM) achieved bond strengths of between 22 and 27 MPa for dentin bonding, which approaches or equals the point of cohesive failure of tooth dentin. High bond strengths of around 23-26 MPa were also achieved with that two component priming system for bonding to tooth enamel. (See, e.g., J. Esthetic Dentistry article, Hydrophilic Primer Adhesive System and Optional Hydrophobic Resin).

C. Single Component Primer Systems

Additionally, there have been reported certain "one-component" or "single-step" dental bonding systems. See, for example, Blackwell et at. U.S. Pat. Nos. 4,657,941 and 4,816,495 and Huang et at. U.S. Pat. No. 4,966,934 all of which are assigned to Dentsply Research and Development Corporation (hereinafter also collectively referred to as the Dentsply patents) and Bunker U.S. Pat. No. 5,304,585.

The Bunker et al. system is reported as involving polymerizable phosphoric acid ester adhesives. Such compositions are generally disclosed therein as capable of being packaged with polymerization initiators in the presence of polymerization inhibitors and other compounds in one package. (See '585 patent, col. 10, line 31 to col. 11, line 8). However, such one-component packaging is not exemplified in the '585 patent. Instead, a two-component was tested in Example 1 of that patent, involving admixing of the polymerization initiator sodium benzenesulfinate first component with the phosphorous ester monomer second component immediately before application to the tooth substrate. Bunker et al. also reported relatively low bond strength to dentin of around 9 MPa. (See '585 patent, col. 12, lines 16-42).

The Dentsply patents also disclose alleged one-component dentin and enamel bonding primer and adhesive systems. Such systems are reported as based inter alia on phosphorous-containing adhesion promoter compounds. However, the phosphorous-based bonding systems disclosed in the examples of '941 and '495 patents all gave relatively low bond strengths of 8.39 MPa or less.

The dipentaerythritol pentaacrylate phosphoric acid ester-based (PENTA) bonding systems disclosed in the '934 patent were reported as generating higher dentin bond strengths in the range of 10-27 MPa. (See '934 patent Example 10). However, also reported therein is data showing that the higher reported bond strength systems were not stable over time, with the 27 MPa strength system reported as decreasing to around 10 MPa or less after 1-2 weeks storage of the system at elevated temperatures. (See '934 patent, Table VIII). Moreover, the higher bond strengths reported in the '934 patent were in actuality two-component systems in which a second commercial, unfilled adhesive bonding resin component was used after application of the phosphorous primer composition. (See Example 4 and Example 10 at Col. 17, line 60-Col. 18, line 53 and Tables IX and X). The "most promising" PENTA-based bonding systems disclosed in the '934 patent were further tested with that additional second adhesive component and step which were reported to provide bonding strengths from about 17 to 20 MPa. (See Table X). In all three Dentsply patents, the primer curing system was reported as light-curing done after either application of the composite resin material and/or after application of a separate adhesive resin. (See Example 4 of '941, 495 and 934 patents).

U.S. Pat. No. 4,525,256 discloses certain one component photopolymerizable resins containing certain tertiary amine accelerators. However, such compositions are composite (filled) resins, and not dental primer or adhesive compositions. (See '256 patent, Examples 1-3).

U.S. Pat. No. 5,295,824 discloses inter alia plastic orthodontic devices with a "shelf-stable" monomeric adhesive layer pre-coated and "solvated" into the plastic device. The bond strengths reported therein are about 10-20 kg, which if meant to be kg/cm$^2$, translate to rather low levels of around 2-4 MPa.

PCT application publication No. WO/93/02630 discloses an adhesive-coated orthodontic bracket. The bracket's adhesive layer comprises ethoxylated diglycidyimethacrylate of Bisphenol A (Bis-GMA), Bis-GMA and/or other monomers and photo-initiator catalysts and inhibitors. The bond strength of such pre-coated brackets were reported to be in the range of 54-104 kg/cm$^2$ (about 5-10 MPa).

D. Bond Strength and Etching Systems

In general, the three step process of etching/rinsing, applying a primer(s), followed by an adhesive, and thereafter followed by a restorative resin has been reported in the literature as the "gold standard" of achieving high bond stability and durability in a dental restoration bonded to dentin. De Munck et al., J. Dent. Res. 84(2):118-124 (2005). However, three step process restorations are reported to be more labor intensive and technique sensitive, and the technique used can significantly influence the resultant bond strength. Id. Nonetheless, reported laboratory results show that three step etch and rinse systems provide in an average initial dentin microtensile bond strength (μTBS) that is higher than that reported for acid etched and self-etched two-step adhesive systems. Id. Self-etched single component systems were reported to have the lowest initial microtensile bond strengths. Id.

Commercially available single-component self-etching bonding systems are reported as being promoted for use primarily for ease of use and low technique sensitivity, as well as good performance in class V clinical trials. Inoue et al.; J. Dent. Res 84(12):1160-1164 (2005). However, aside from the relatively low initial dentin and enamel bond strength, self-etch single-component systems employing functional acidic methacrylate monomers with water that are stored together in a single bottle have been reported to degrade via hydrolysis during storage. Nishiyama et al., J. Dent. Res. 85(5):422-426 (2006) (describing such simplified self-etch adhesives as having "poor shelf lives"). Further, such degradation has been reported to occur as early as one month from the date of manufacture when kept at 25° C. Id.

E. Bond Strength and Hydrophilicity

Apart from initial bond strength, recent studies have tested the bond strength of various resins when exposed to conditions approximating those experienced in vivo over time. In particular, it has been reported that resins formed from relatively hydrophilic monomers results in a substantially weaker bond strength after cured, largely due to hydrolysis, elution, and the formation of water trees within the hybrid layer. Yiu C K, J. of Biomaterials (25):5789-5796 (2004). Those, studies report that the greatest absorption of water in hydrophilic compounds occurs within the first day of exposure to water. Id. In addition, hydrophilic acidic resins were reported to show the greatest decrease in bonding strength within the first month of exposure to water. Id. Recent studies suggest that some commercial single-step dental bonding systems are hydrophilic and have their greatest water-absorption during the first few weeks of storage in water. Malacarne J, Dent. Mater. (22): 973-980 (2006).

Therefore, an improved two or three-step restoration system showing higher initial bond strength and improved bond stability and durability over time would be appreciated by those in the art.

DESCRIPTION

According to the present invention, an improved dental adhesive and restoration system is disclosed. In particular, the present invention relates to one part or two part self-etching primer adhesive system that is compatible with light-cured, self-cured, and dual-cured materials and which does not require the mixing with an additional activator applied in an additional bottle. In addition, the primer adhesive systems disclosed herein relate to a one part or two part self-etching primer adhesive system that displays improved penetration into dentin and enamel, thereby forming a better hybrid layer and better bonding strength.

The present invention relates to a one-step self-etching primer adhesive system having a Part 1 component comprising a polymerizable phosphate ester componenet, a relatively hydrophilic polymerizable monomer component, a polymerizable acidic monomer component, a multi-(meth)acrylate cross-linking component, a relatively hydrophobic polymerizable monomer component, a tertiary amine component and a light cure initiator component, and a Part 2 component comprising deionized water, an aryl sulfinate salt, optionally a coloring agent, and an alcohol solvent.

In particular, a presently preferred embodiment of the present invention relates to a one-step self-etching primer adhesive system having a Part 1 component comprising bisphenol A diglycidylether methacrylate phosphate ("BisGMA phosphate"), 2-hydroxyethyl-methacrylate ("HEMA") as a relatively hydrophilic component, BPDM as an acidic polymerizable monomer component, dipentaerythritol pentaacrylate ("DPEPA") as across-linking component, bisphenyl A diglycidylmethacrylate ("BisGMA") as a relatively hydrophobic monomer component, ethyl-4-dimethylaminobenzoate ("EDMAB") as a tertiary amine component and camphorquinone ("CQ") as a light cure initiator, and a Part 2 component comprising deionized water, an aryl sulfinate salt, thymol blue coloring agent and denatured ethanol as a solvent component. An aryl sulfinate salt according to the present application may include sodium benzenesulfinate, a substituted benzene ring, toluenesulfinate, bromobenzenesulfinate, and nitrobenzenesulfinate.

According to one exemplary embodiment, the present invention having a Part 1 component may comprise about 20% BisGMA phosphate (by weight), about 30% HEMA (by weight), about 8% BPDM (by weight), about 10% DPEPA (by weight), about 31% BisGMA (by weight), about 0.5% EDMAB (by weight), and about 0.5% CQ (by weight), and a Part 2 component comprising about 17.6% deionized water (by weight), about 2.4% sodium bezenesulfinate (by weight), about 0.2% thymol blue (by weight), and about 80% denatured ethanol (by weight).

When the part 1 component and part 2 component are mixed and applied to a prepared dental surface comprising dentin and/or enamel, the following bond strengths are observed as compared to other commercial systems as shown in Table 1. It will be appreciated that testing using the microtensile strength was performed similarly to that described in Sano et al., Dent Mater 10: 236-240 (1994), and testing using the "Ultradent Jig" was performed using the Ultradent technique as described in Pashley et al., Dent. Mater. 11: 117-125 (1995). Testing using the Gel Cap method was performed substantially as prescribed in Drummond et al., Vol 32, Iss. 4, 533-541 (1998), and as otherwise known in the art.

TABLE 1

MICROTENSILE SHEAR BOND STRENGTH ("μ-TBS") COMPARISON WITH LIGHT CURE RESINS-DENTIN AS SUBSTRATE (MPa)

|  | μ-TBS (SD) | Ultradent Jig (SD) | Gel Cap #5 |
|---|---|---|---|
| 1-Step SE |  |  |  |
| Present Invention Bonding Agent | 42.2 (11.9) | 36.3 (5.5) | 18.7 (2.3) |
| iBond | 52.0 (15.1) | 20.5 (8.8) | N/T |
| Xeno III | 36.4 (15.8) | 31.8 (7.6) | 16.5 (4.9) |
| Adper L-Pop | N/T | 21.4 (4.5) | 11.9 (3.1) |
| 2-Step SE |  |  |  |
| Present Invention + Liner | 50.7 (13.4) | 38.9 (4.3) | 20.9 (2.7) |
| Clearfil SE | 59.4 (13.1) | 35.2 (5.9) | 21.3 (1.4) |

In addition to the favorable bond strengths shown by the primer adhesive according to the present application, the primer adhesive disclosed herein further shows compatibility with self-cure and dual-cure bonding systems as shown by the bond strengths outlined in Table 2 below.

In addition, it will be appreciated that bond strength of the present invention with a liner containing HEMA (such as ALL-BOND® D/E Resin). The resin or composite for the liner also optionally comprises a filler such as radiopaque filler. The bond strength of the present invention was compared to a conventional two-step self-etch system such as Clearfil SE as shown in Table 1.

TABLE 2

BONDING STRENGTH WITH SELF-CURE COMPOSITES SHEAR BOND TEST USING ULTRADENT JIG-DENTIN SUBSTRATE (MPa)

|  | Xeno III (SD) | Present Invention (Part 1 and 2) (SD) | Present Invention (Part 1 and 2) + Liner (SD) |
|---|---|---|---|
| Bisfil 2B SC | 0.0 (0.0) | 38.2 (6.6) | 36.0 (7.6) |
| C & B SC | 0.0 (0.0) | 31.0 (5.1) | 36.7 (5.8) |
| DuoLink SC | 0.0 (0.0) | 36.7 (7.9) | 37.2 (5.9) |
| DuoLink LC | 37.3 (6.9) | 36.5 (5.2) | 40.0 (5.8) |

It will be appreciated by those in the art that the self-etch adhesive system shows compatibility and bond strength with self-cure systems, unlike other commercial self-etch single-step primer adhesive systems. It will be further appreciated that the adhesive system disclosed herein as a one-step system may be used as a two-step system by providing a resin used as a liner by coating the primer adhesive system, as known in the art. Contrary to other products in the market, the present primer system offers the option of using system as a single-step self-etch or as a two-step self-etch, accomplishing both easiness of use and reliability into one single product. When used as a single-step self-etch, the present invention delivers chemical compatibility with self- and dual-cured composites, without the need to mix, use or purchase additional solutions. Self- and dual-cure resin cements or restorative composites can be placed directly on cured single-layer of the primer and adequate coupling can be expected as shown above. In addition, for reduced permeability across the adhesive layer, the present invention offers the clinician the possibility of a two-step self-etch application mode without the need to purchase another product. For example, the present invention can be used with a second-step resin liner that forms a non-acidic, filled and radiopaque layer for improved compatibility with resin composites, regardless of the mode of activation.

What is claimed is:

1. A self-etching dental adhesive system comprising:
  a. a first portion and a second portion operable to be mixed prior to application to a dental surface, wherein
    i. the first portion comprises bisphenol diglycidyl-methacrylate phosphate, 2-hydroxyethyl-methacrylate ("HEMA"), biphenyl dimethacrylate ("BPDM"), dipentaerythritol pentaacrylate ("DPEPA"), bisphenyl A diglycidylmethacrylate ("BisGMA"), ethyl-4-dimethyl-aminobenzoate ("EDMAB") and camphorquinone ("CQ"); and
    ii. the second portion comprises deionized water, an aryl sulfinate salt, thymol blue, and ethanol,
    iii. wherein the resultant adhesive system is compatible with self-cure resins or self-cure composites.

2. The self-etching dental adhesive system of claim 1, wherein the aryl sulfinate salt is selected from the group consisting of: a benzene sulfinate sodium salt and a substituted benzene sulfinate salt.

3. The self-etching dental adhesive system of claim 1, wherein the aryl sulfinate salt is sodium benzenesulfinate.

4. The self-etching dental adhesive system of claim 1, wherein the first portion comprises about 20% bisphenol diglycidylmethacrylate phosphate (by weight), about 30% HEMA (by weight), about 8% BPDM (by weight), about 10% DPEPA (by weight), about 31% BisGMA (by weight), about 0.5% EDMAB (by weight), and about 0.5% CQ (by weight).

5. The self-etching dental adhesive system of claim 4, wherein the second portion comprises about 17.6% deionized water (by weight), about 2.4% sodium bezenesulfinate (by weight), about 0.2% thymol blue (by weight), and about 80% denatured ethanol (by weight).

6. The self-etching dental adhesive system of claim 1, wherein the second portion comprises about 17.6% deionized water (by weight), about 2.4% sodium bezenesulfinate (by weight), about 0.2% thymol blue (by weight), and about 80% denatured ethanol (by weight).

7. The self-etching dental adhesive system of claim 1, further displaying a shelf life greater than three months.

8. A self-etching dental adhesive system comprising:
  a. a first part and a second part operable to be mixed prior to application to a dental surface, wherein
    i. the first portion comprises about 20% bisphenol diglycidylmethacrylate phosphate (by weight), about 30% HEMA (by weight), about 8% BPDM (by weight), about 10% DPEPA (by weight), about 31% BisGMA (by weight), about 0.5% EDMAB (by weight), and about 0.5% CQ (by weight); and
    ii. the second portion comprises about 17.6% deionized water (by weight), about 2.4% sodium bezenesulfinate (by weight), about 0.2% thymol blue (by weight), and about 80% denatured ethanol (by weight).

9. The self-etching dental adhesive system of claim 8, wherein the self-etching dental adhesive system is compatible with self-cure resins or self-cure composites.

10. The self-etching dental adhesive system of claim 8, wherein the self-etching dental adhesive system is compatible with light-cure resins or light-cure composites.

11. The self-etching dental adhesive system of claim 9, further displaying a shelf life greater than three months.

12. The self-etching dental adhesive of claim 1, wherein the aryl sulfinate salt is selected from the group consisting of: toluenesulfinate, bromobenzenesulfinate and nitrobenzenesulfinate.

\* \* \* \* \*